US009867677B2

(12) United States Patent
Fulkerson

(10) Patent No.: US 9,867,677 B2
(45) Date of Patent: Jan. 16, 2018

(54) DENTAL MEMBRANE OR TISSUE PLACEMENT FORCEPS

(71) Applicant: Brad Fulkerson, Portsmouth, NH (US)

(72) Inventor: Brad Fulkerson, Portsmouth, NH (US)

( * ) Notice: Subject to any disclaimer, the term of this patent is extended or adjusted under 35 U.S.C. 154(b) by 115 days.

(21) Appl. No.: 14/626,438

(22) Filed: Feb. 19, 2015

(65) Prior Publication Data
US 2015/0351869 A1 Dec. 10, 2015

Related U.S. Application Data

(60) Provisional application No. 62/009,535, filed on Jun. 9, 2014.

(51) Int. Cl.
*A61C 3/10* (2006.01)
*A61C 8/02* (2006.01)

(52) U.S. Cl.
CPC .............. *A61C 3/10* (2013.01); *A61C 8/0006* (2013.01)

(58) Field of Classification Search
CPC .............. A61B 17/50; A61B 2017/505; A61B 2018/1462; A61B 10/06; A61B 17/30; A61B 17/06061; A61B 2017/1125; A61B 17/1606; A61B 17/22031; A61B 17/28; A61B 17/29; A61B 2018/0225; A61B 18/085; A61B 18/1442; A61B 18/1445; A61C 3/00; A61C 3/14; A61C 3/16; A61C 3/10
See application file for complete search history.

(56) References Cited

U.S. PATENT DOCUMENTS

| | | | |
|---|---|---|---|
| 8,351 A | 9/1851 | Burch | |
| 354,863 A | 12/1886 | Hughes | |
| 732,288 A | 6/1903 | Felsch | |
| 1,007,824 A * | 11/1911 | Trosper | A61C 3/14 294/902 |
| 2,531,126 A | 11/1950 | Hawkinson | |
| 4,449,928 A * | 5/1984 | von Weissenfluh | A61C 5/50 433/229 |
| 4,671,283 A * | 6/1987 | Hoskin | A61B 17/30 606/211 |
| 4,747,404 A * | 5/1988 | Jampel | A61F 2/1664 606/107 |
| 5,011,491 A | 4/1991 | Boenko | |
| 5,057,016 A | 10/1991 | Lukase | |
| 5,464,405 A * | 11/1995 | Fujitsu | A61B 18/1442 606/211 |
| 6,322,363 B1 * | 11/2001 | Beecher | A61C 3/10 433/159 |
| D719,655 S * | 12/2014 | Lim | D24/153 |

(Continued)

*Primary Examiner* — Nicholas Lucchesi
*Assistant Examiner* — Drew Folgmann
(74) *Attorney, Agent, or Firm* — Andrus Intellectual Property Law, LLP

(57) ABSTRACT

A dental membrane placement forceps which includes a thin spatula on the tip of one arm of the forceps. The spatula has a concave inward face juxtaposed the tip on the opposing forceps arm and is oriented substantially perpendicular to the direction in which the opposing forceps tips move inward toward one another to grip the object (i.e., the gripping plane). The concave inward face of the spatula is concave in one direction. The forceps is useful for placing flat, flexible materials such as a membrane used for regenerative osseous surgery in dentistry.

19 Claims, 3 Drawing Sheets

(56) References Cited

U.S. PATENT DOCUMENTS

| | | | | |
|---|---|---|---|---|
| 2002/0106609 | A1* | 8/2002 | Palermo | A61C 3/10 |
| | | | | 433/159 |
| 2005/0070955 | A1* | 3/2005 | Young | A61B 17/30 |
| | | | | 606/210 |
| 2005/0255421 | A1* | 11/2005 | Michaelson | A61C 3/10 |
| | | | | 433/4 |
| 2007/0197066 | A1* | 8/2007 | Chang | B26B 27/007 |
| | | | | 439/136 |
| 2007/0254263 | A1* | 11/2007 | McDonald | A61C 5/127 |
| | | | | 433/149 |
| 2008/0312669 | A1* | 12/2008 | Vries | A61B 17/0493 |
| | | | | 606/148 |
| 2011/0027754 | A1* | 2/2011 | Golden | A61C 3/14 |
| | | | | 433/159 |
| 2013/0224682 | A1* | 8/2013 | Mueller | B25B 9/02 |
| | | | | 433/162 |
| 2013/0341941 | A1* | 12/2013 | Stayton | B25B 9/02 |
| | | | | 294/99.2 |
| 2015/0282871 | A1* | 10/2015 | Wang | A61B 18/1442 |
| | | | | 606/52 |

\* cited by examiner

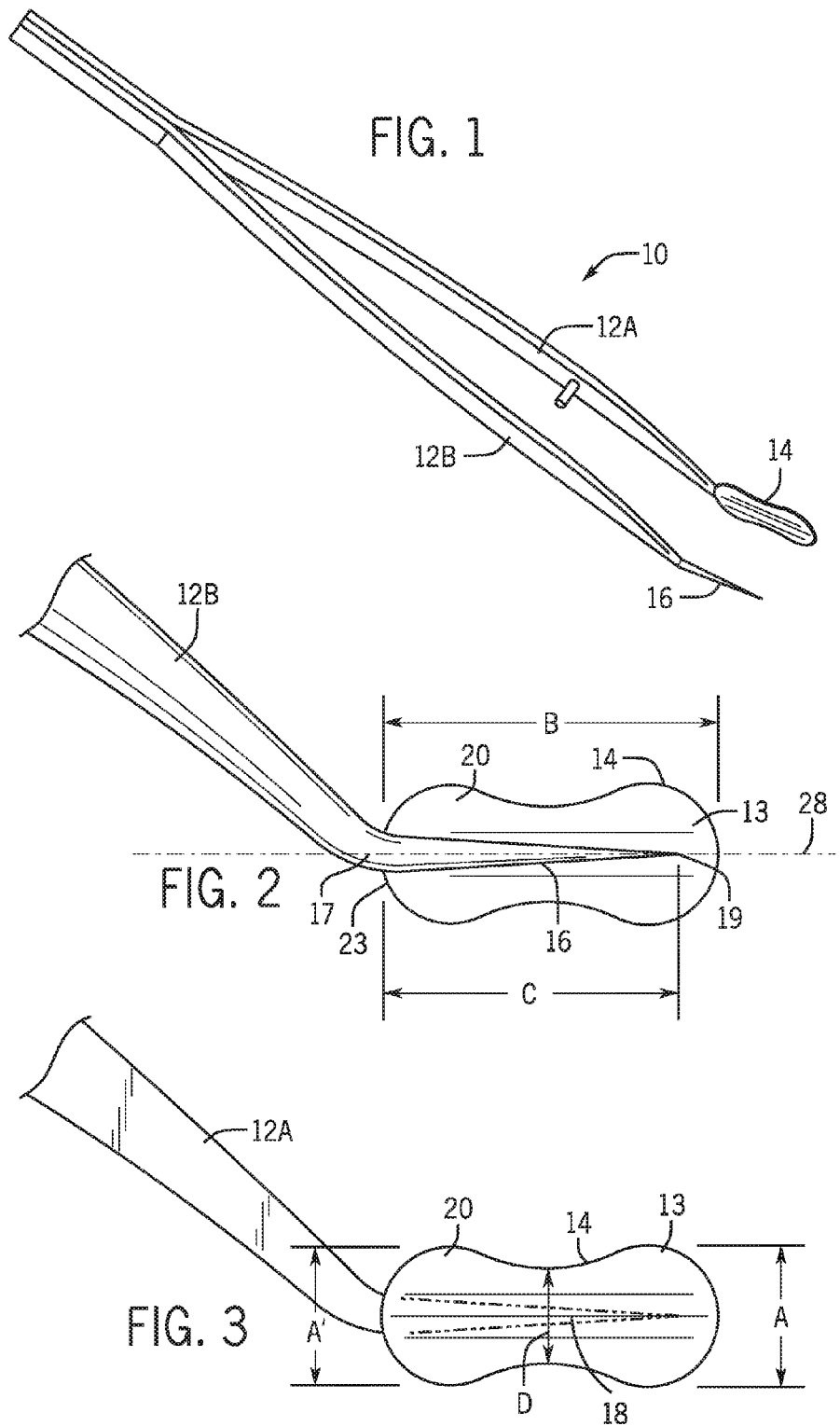

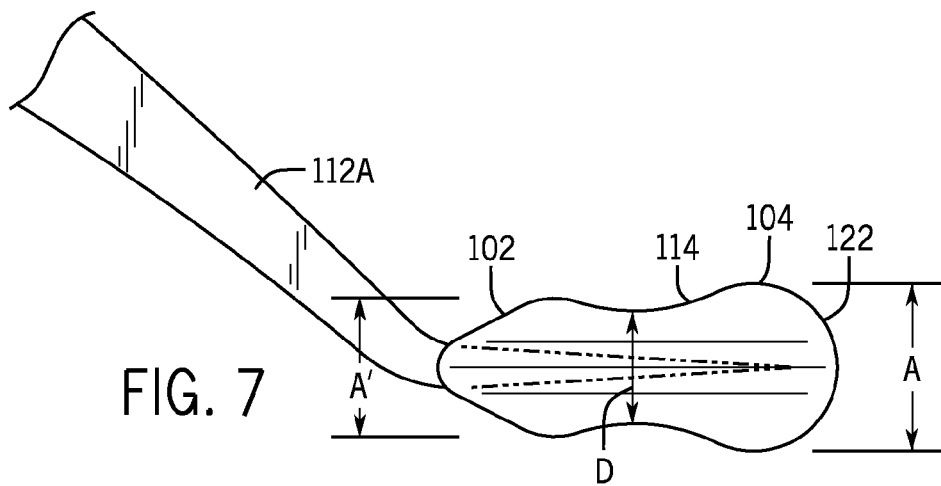
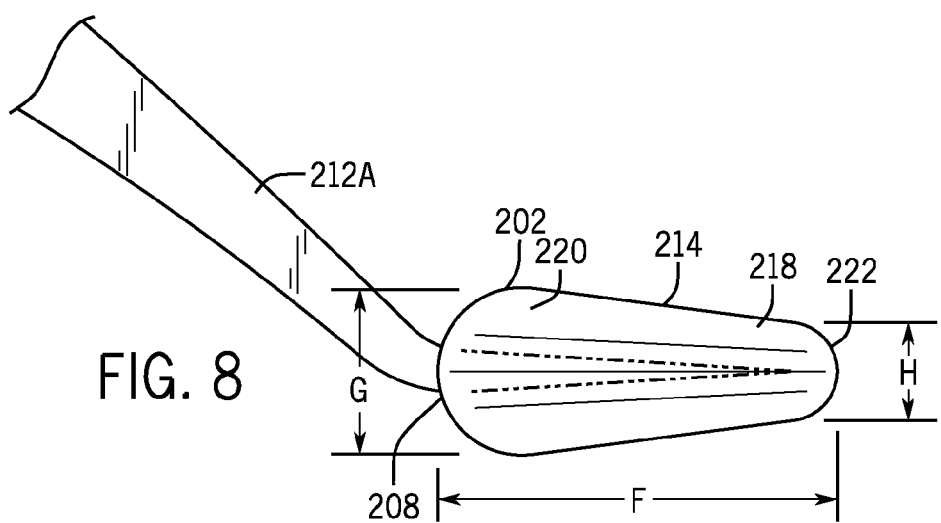

DENTAL MEMBRANE OR TISSUE PLACEMENT FORCEPS

FIELD OF THE INVENTION

The invention relates to forceps designed primarily to assist in the placement of membranes during regenerative osseous surgery and secondarily to aid in placement of other flat and flexible materials during dental surgery such as autogenous connective tissue grafts.

BACKGROUND OF THE INVENTION

During various regenerative osseous surgeries in dentistry, a membrane is often placed to block out soft tissue growth and invagination into bone graft sites. This is necessary because bone growth occurs at a slower rate than soft tissue growth during the healing process. By covering the selected bone graft material with a membrane (resorbable or non-resorbable), the faster growing soft tissue is blocked from growing into the graft, thereby allowing the slower growing bone cells to infiltrate into the graft and ideally allow for a greater amount of bone regeneration. Dental bone grafting is most commonly done in association with site development for dental implants but can be done in other applications where bone preservation or regeneration is needed. These applications include, but are not limited to, socket preservation following dental extractions or bone regeneration to correct bone loss related to periodontal disease, trauma, or long term missing teeth.

Typically, after the bone graft has been appropriately placed at the desired site, a membrane is gently placed, using a tissue forceps or college pliers (which is not specifically designed for membrane placement), between gingival tissue (under the periostium) and the bone graft. The membrane can be secured into place with sutures, tacks, or screws if needed. Primary closure is achieved over most membranes although is not always indicated with some non-resorbable membranes.

Membranes are normally provided from the manufacturer in a square, rectangular or oval shape and are cut to a preferred shape for placement. A horizontal peanut shape is effective for placement over grafted extraction sites between two teeth.

Sometimes the space in which the membrane must be placed is quite narrow, which often causes ideal placement to be difficult. As the membrane is placed between the periostium and bone graft, the corners have a tendency to fold up and over toward the periostium, leaving the deeper portions of the graft potentially exposed to soft tissue invagination. Similarly, as flapless and less invasive approaches are becoming more widely advocated, so is this issue of passing a membrane through tight spaces without having the edges fold. Existing tissue forceps, which are currently being used for membrane placement, need significant modification to be made more specific for membrane placement in order to prevent membrane folding on placement.

The gripping and placing other flat, flexible materials such as autogenous connective tissue grafts during oral surgery can also be difficult for similar reasons.

SUMMARY OF THE INVENTION

In one aspect, the invention pertains to a forceps especially designed for placing membranes for regenerative osseous surgery in dentistry, or placing other flat, flexible materials during dental or oral surgery procedures such as connective tissue grafts. When used for placing membranes in regenerative osseous surgery, the forceps includes a pair of forceps arms with a forceps tip on one of the arms and a thin, spatula located on the other arm. The membrane is held between the forceps tip and the inward face of the spatula when the arms are pushed together to a closed position. The spatula is oriented substantially perpendicular to the direction in which the opposing tip and spatula move inward toward one another to grip the membrane (i.e. substantially perpendicular to the gripping plane). The inward spatula face is concave in one direction and forms a trough for the membrane juxtaposed the opposing tip. Desirably, the deepest region of the trough lies in the forceps gripping plane which facilitates steady holding of the membrane during placement. The amount of curvature and the cross sectional geometry can be customized depending on surgical site anatomy. The shape of the membrane is cut to the same or similar outline as the spatula face, such that the spatula can be used as a template to cut the membrane. The geometry of the spatula face can have different forms depending on its particular use or surgical site. As mentioned, a horizontal, peanut shape is effective for membrane placement over grafted extraction sites between two teeth (FIG. 2). Similarly an "ice cream cone" or tooth socket shape spatula tip can be used for placement along a missing wall of a single rooted tooth (FIG. 8). Other shapes may be used as well (FIG. 7). It is preferred that the front edge of the spatula surface extend forward from the front edge of the opposing tip and that the front edge be curved (FIG. 2).

The forceps are preferably reusable, and made of a material that is autoclavable such as stainless steel. While the forceps are described primarily as useful for placing membranes during regenerative osseous surgery in dentistry, the forceps can also be used to place other flat, flexible materials during other dental or oral surgery procedures, e.g. autogenous connective tissue grafts, or possible other types of surgery as well.

It is contemplated that multiple forceps having different spatula configurations may be included in a kit. Such a kit may include forceps that are right-side and left-side specific or neutral for the anterior region of the mouth. Further, the spatula faces can have different sizes and/or shapes as previously described. Similarly, the angle of the tip and spatula from the forceps arm can vary as well depending on the area of the mouth to be worked on.

In another aspect, the invention pertains to methods of placing membranes for regenerative osseous surgery in dentistry, or placing other flat, flexible materials during dental or oral surgery procedures, using the forceps with spatula having the concave inward face described above.

BRIEF DESCRIPTION OF THE DRAWINGS

FIG. 1 is a perspective view of a membrane placement forceps for regenerative osseous surgery in dentistry constructed in accordance with a first embodiment of the invention.

FIG. 2 is a side elevation view showing the tip on one of the forceps arms in front of an inward face of the peanut-shaped, concave spatula on the other forceps arm.

FIG. 3 is a side elevation view showing the inward face of the peanut-shaped, concave spatula in FIG. 2, with the closed position of the opposing forceps tip on the concave spatula shown in phantom.

FIG. 7 is a view similar to FIG. 3 illustrating another embodiment in which the geometry of the spatula is different.

FIG. 8 is another view similar to FIG. 3 illustrating another embodiment in which the geometry of the spatula is different.

DETAILED DESCRIPTION OF THE DRAWINGS

Figure 4:
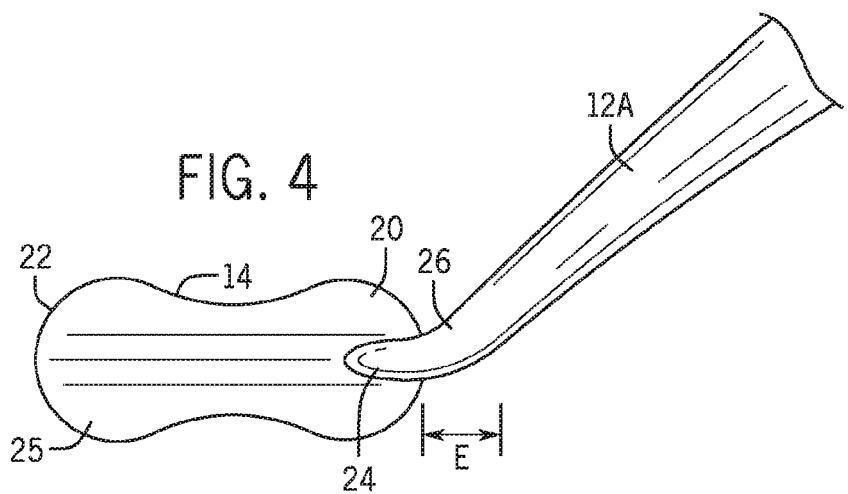
FIG. 4 is a rear elevational view of the peanut-shaped, concave spatula shown in FIGS. 2 and 3.
Figure 5:
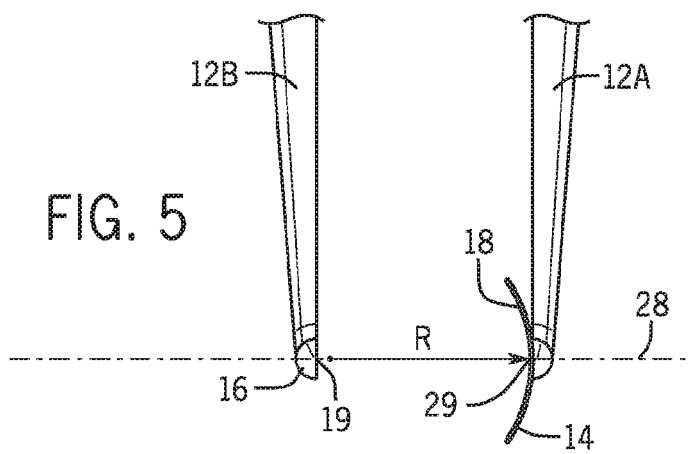
FIG. 5 is a front elevation view taken perpendicular to the gripping plane of the forceps.
Figure 6:
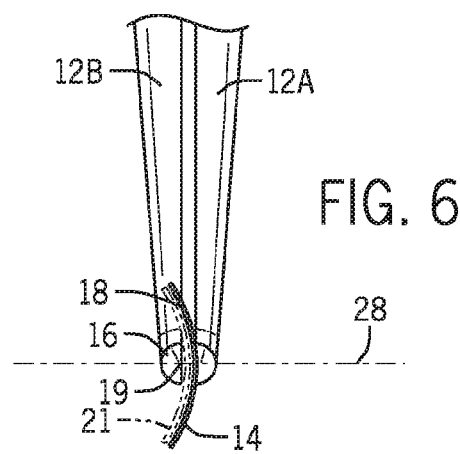
FIG. 6 is a schematic view illustrating a membrane being held between the concave inward face of the spatula and the opposing forceps tip.

FIGS. 1 through 6 illustrate a membrane placement forceps 10 constructed in accordance with a first embodiment of the invention. The forceps 10 is held in the hand of the surgeon and includes opposing arms 12A and 12B. A broad, thin spatula 14 is located at the distal end of forceps arm 12A to provide maximum contact with the membrane 21 (FIG. 6) during insertion or placement over a dental graft site. The tip 16 on the opposing arm 12B is the same or similar to a conventional forceps tip. While FIG. 1 shows a forceps having standard forceps arms 12A, 12B, the spatula 14 can be implemented on other types of forceps. For example, a scissors style forceps can be used in accordance with the invention and may provide for easier withdrawal of the forceps after placement into tight spaces. In use, the membrane 22, FIG. 6, is cut to match the dimensions of the spatula 14, e.g. using the spatula 14 as a template. Then, the membrane 21 is gripped between a concave, inward face 18 of the spatula 14 and the opposing tip 16, see FIG. 6.

Referring in particular to FIGS. 2 and 3, the spatula 14 has peanut-like geometry which as mentioned is particularly well suited for placing membranes over grafted tooth extraction sites between two teeth. The front edge 22 of the spatula 14 should have rounded corners to prevent the spatula 14 and the membrane 21 from catching on soft tissue which could result in folding or a tear in the overlying tissue. The spatula 14 is made thin enough to allow passage into tight spaces between the tissue and bone. A suitable thickness for the distal end 13 of the spatula 14 is 0.25 mm, and the thickness should be no greater than about 0.5 mm in order to avoid excess interference in tight spaces. Ideally, the thickness of the spatula 14 is constant from the front edge 22 to the attachment point 24 with the forceps arm 12A, see FIG. 4. However, constant thickness of the spatula 14 is not a necessity, as long as the thickness of the distal end 13 of spatula 14 does not exceed about 0.5 mm. Similarly, the thickness of the tip 16 on the opposing forceps arm 12B should be thin enough to not interfere in small spaces as well. For example, 1.5 mm is a suitable thickness at the base 17 of tip 16, and 0.5 mm to 1.0 mm is a suitable thickness at the point 19 of tip 16.

FIGS. 2 and 3 designate dimensions for molar and pre-molar/anterior, peanut shaped spatulas 14. The maximum height of the distal portion 13 of the peanut-shaped spatula 14 is designated by arrow A. The maximum height of the proximal portion 20 of the peanut-shaped spatula 14 is designated by arrow A'. Desirably, the height A of the distal portion 13 is slightly greater than the height A' of the proximal portion 20 of the spatula 14. The minimum height of the spatula 14 between the proximal portion 20 and the distal portion 13 is designated by arrow D. The overall length of the spatula 14 is designated by arrow B. Arrow C designated the longitudinal distance from the rear or proximal edge 23 of the spatula 14 to the point 19 of the opposing tip 16 (measured with the forceps 10 closed.) The front edge 22 of the spatula 14 extends forward of the point of the tip 16 on the opposing arm 12B. This enables the front edge 22 of the spatula 14 to place the membrane into tight spaces allowing direct contact of the membrane to bone at the placement point without interference from the opposing forceps arm 16. Exemplary dimensions (A, A', B, C, and D) for spatulas 14 designed for molar and pre-molar procedures are set forth in Table 1.

TABLE 1

Exemplary Dimension for Molar and Premolar Spatulas

| | Molar size | Premolar Anterior | Range |
|---|---|---|---|
| A: | ~8.5 mm | ~7.0 mm | ~6.5-9.0 mm |
| A': | ~8.0 mm | ~6.5 mm | 6.0-8.5 mm |
| B: | ~20 mm | ~20 mm | |
| C: | ~18 mm | ~18 mm | |
| D: | ~6.5 mm | ~5.0 mm | 4.5-7.0 mm |

FIG. 4 illustrates the rear face 25 of the spatula 14. The configuration of how the rear face 25 is attached to the forceps arm 12A can vary, however, it is preferred that the connection point 24 be on the proximal end 20 of the spatula 14. This enables the spatula 14 to remain thin over substantially its entire length. In the embodiment shown in FIG. 4, the bend 26 in the forceps arm 12A is selected so that the spatula 14 extends forward of the bend 26 in alignment with the opposing tip 16, and the length of the bend 26 (i.e., designated distance E) is about 3.0 to 4.0 mm so the presentation and alignment of the spatula 14 is commensurate with that of the opposing tip 16.

FIG. 5 is a front elevation view taken perpendicular to the gripping plane 28 of the forceps 10. The gripping plane 28 is shown in FIGS. 2 and 6 in addition to FIG. 5. The inward face 18 of the spatula 14 is juxtaposed the tip 16 on the opposing forceps arm 12B and is oriented substantially perpendicular to the direction in which the opposing arms 12A, 12B move inward toward one another (i.e., substantially perpendicular to the gripping plane 28). The spatula 14 and its inward face 18 are desirably concave in one direction with respect to the tip 16 on the opposing arm 12B. In FIG. 5, the concave surface of the inward face 18 is in the shape of a circular arc having a curvature radius R with the center axis 30 for the curvature radius R in the gripping plane 28, but this is not necessary in other embodiments of the invention. In embodiments where the inward face 18 has a circular cross section, the curvature radius R can vary from a slight curve (i.e. about 10 cm) to an aggressive curvature radius R of about 2.5 cm as depicted in FIG. 5. While some amount of concavity in one direction is important for reliably maintaining the membrane 21 steady during placement, the amount of concavity and the cross sectional geometry of the concavity will depending primarily on the appropriate fit for the respective anatomical features of the patient.

FIG. 6 shows a membrane 21 gripped between the inward face 18 of the spatula 14 and the tip 16 on the opposing arm 12B of the forceps 10. The inward concave spatula face 18 forms a trough for the membrane 21. The deepest region 29 (FIG. 5) of the trough 18 lies in the forceps gripping plane 28. The inward face 18 of the spatula 14 provides maximum contact with the membrane 22 during insertion over the graft site. As mentioned, the membrane 21 is desirably cut in a horizontal peanut-shape commensurate with the shape of the spatula 14. As the membrane 22 is held between the inward face 18 of the spatula 14 and the opposing forceps tip 16, the broad inward spatula face 18 covers the rounded corners of the membrane 22 and helps prevent them from catching on soft tissue when the membrane 21 is inserted over the graft, and thereby substantially reduces the possibility unwanted folding of the membrane 21. As discussed previously, the spatula is made thin enough to allow passage into tight spaces between tissue and bone, and the concave shape provides the membrane 21 more rigidity during placement and also more accurately follows the anatomy of the buccal or lingual plate. As also discussed above, the opposing tip 16 is narrow and shorter than the spatula 14 which allows maximal contact of the membrane 22 with the bone graft upon removal of the forceps 10, thereby helping it to stay in proper position.

The spatula 14 can be made in a variety of sizes and shapes to accommodate commonly used membrane sizes/shapes (i.e. tooth/socket specific for molars, premolars, incisors, etc.). The forceps 10 and spatula 14 can also be made right and left-side specific, or have a neutral configuration for the anterior region of the mouth. As discussed above, the forceps 10 can have a tweezers configuration as shown in FIG. 1 or other configurations such as a scissors configuration. In addition, the angle between the opposing tip 16 and the forceps arm 12B and the orientation of the spatula 14 and forceps arm 12A can be varied from that shown in the drawings or can be eliminated (e.g. straight) depending on the surgical site anatomy and location in the mouth.

FIG. 7 illustrates another embodiment of the invention in which the geometry of the spatula 114 has been modified compared to that shown in FIGS. 1 through 6. The dimensions A, A', B, C and D in the embodiment shown in FIG. 7 are substantially the same as in FIGS. 2 and 3. In FIG. 7, the distal end 104 and the front edge 122 of the spatula 114 are substantially the same as the spatula 14 described in FIGS. 1 through 6; however, the proximal end 102 of the spatula 114 has been modified to reduce the size and roundness of the proximal end 102. Such spatula geometry may be useful for a particularly tight space where, for example, adjacent teeth are tipped or angled thereby tending to interfere with the proximal end 20 of the spatula shown in FIGS. 2-4 and prevent placement of the spatula tip or front edge 22 to the desired location.

FIG. 8 illustrates another embodiment in which the geometry of the spatula 214 has been modified to work better for membrane placement into sites where a "cone shaped" single rooted tooth has been extracted and is missing a buccal or lingual plate of bone. In FIG. 8, the proximal portion 220 is noticeably higher than the distal portion 218. The front edge 222 and the rear edge 208 at the proximal end 202 are round. In an exemplary embodiment, the height G of the proximal portion 220 is about 5.0 mm, and the height H of the distal portion 218 is about 2.0 mm, which are both less than the heights A and A' in the previous exemplary embodiments. In addition, the overall length F of the spatula 214 is about 20.0 mm which is slightly greater than the length B in the previous exemplary embodiments to allow placement to the apex of the extracted tooth.

The forceps 10 can be made of an autoclavable material such as stainless steel, although the forceps could be made of disposable material such as polystyrene or polypropylene. It is contemplated that the spatula 14 will normally be constructed as an integral component of the forceps 10; it may be desirable in some circumstances to manufacture the spatula as a fitting that is permanently or removably attached to a conventional preexisting forceps or forceps especially made for removable spatulas.

While the invention has been described above with respect to the placement of a membrane 21 during regenerative osseous surgery, the forceps as shown or slightly modified can be used to grip other flat, flexible materials during dental or oral surgery such as autogenous connective tissue grafts during periodontal surgery. For example, the forceps 10 and spatula 14 has been found to be quite useful to place such connective tissue grafts without folding into tight places during dental surgery.

Those skilled in the art may recognize that the forceps with the spatula may be useful to place membranes or other flat materials during other types of dental or non-dental surgeries.

What is claimed is:

1. A membrane placement forceps for regenerative osseous surgery in dentistry, the forceps comprising:
a pair of elongated forceps arms activated with finger pressure, the pair comprising a first forceps arm and a second forceps arm attached together at a proximal end and free at a distal end;
a gripping tip on the distal end of the first forceps arm, said gripping tip having a gripping surface extending along a gripping plane from a base of the gripping tip to a front portion of the gripping tip; and
a spatula for assisting in the placement of a membrane to block out soft tissue growth during regenerative osseous surgery, the spatula being statically secured on the distal end of the second forceps arm in a fixed orientation and extending generally in a plane in which the linear direction of the elongated second forceps arm resides, said spatula having an inward face that is concave and facing the gripping surface of the gripping tip on the first forceps arm, the inward face of the spatula having a length from a proximal edge of the spatula to a front edge of the spatula that is greater than a height of the inward face;
wherein said gripping plane passes through the proximal edge and the front edge of the spatula when the forceps are fully closed, and the direction in which the gripping tip moves inward towards the opposing inward face of the spatula lies in the gripping plane and the spatula is straight along the gripping plane when the forceps are fully closed;
further wherein the inward face of the spatula comprises a trough for the membrane and the gripping surface of the gripping tip between the base and the front portion of the gripping tip is adapted to hold the membrane against the trough of the concave inward face of the spatula when the forceps arms are fully closed with the membrane placed on the spatula; and
wherein an included angle of intersection of a first line and second line of a triangle is obtuse, said first line passing through a location along an upper edge of the inward face of the spatula that is a maximum distance from the deepest point of the trough where the inward face crosses the gripping plane and a location where the inward face crosses the gripping plane, and said second line passing through a location along a lower edge of the inward face of the spatula that is a maximum distance from the deepest point of the trough where the inward face crosses the gripping plane and the location where the inward face crosses the gripping plane and further wherein a third line passes through the upper edge and the lower edge such that said first line, second line and third line form said triangle, and said triangle lies in a plane orthogonal to the gripping plane.

2. The membrane placement forceps recited in claim 1 further comprising a first bend between the first forceps arm and the gripping tip and a second bend between the second forceps arm and the spatula, wherein the gripping tip is oriented at an obtuse angle with respect to the first forceps arm and the spatula is oriented at the same obtuse angle with respect to the second forceps arm.

3. The membrane placement forceps recited in claim 1 wherein front edges of the spatula are round when viewed from a side elevation of the forceps.

4. The membrane placement forceps recited in claim 3 wherein the spatula has a proximal portion having a local maximum height of A' and a distal portion having a local maximum height of A, and a minimum height D of the spatula is located between the distal portion and the proximal portion, such that A is greater than D and A' is greater than D.

5. The membrane placement forceps recited in claim 4 wherein the height A is greater than the height A'.

6. The membrane placement forceps recited in claim 3 wherein the spatula also has an outward face that is generally parallel to the inward face and the maximum height of the spatula faces is greater at a proximal end than at a distal end of the spatula.

7. The membrane placement forceps recited in claim 3 wherein a front edge of a spatula surface extends forward from the front portion of the tip on the opposing arm.

8. The membrane placement forceps recited in claim 1 wherein the forceps is autoclavable.

9. The membrane placement forceps as recited in claim 3 wherein the thickness of a distal portion of the spatula is no greater than about 0.5 mm.

10. A forceps for dental surgery comprising:
a pair of elongated forceps arms activated with finger pressure, the pair comprising a first forceps arm and a second forceps arm attached together at a proximal end and free at a distal end;
a gripping tip on the distal end of the first forceps arm, said gripping tip having a gripping surface extending along a gripping plane from a base of the gripping tip to a front portion of the gripping tip; and
a spatula for assisting in the placement of a flexible article during surgery, the spatula being statically secured on the distal end of the second forceps arm in a fixed orientation and extending generally in a plane in which the linear direction of the elongated second forceps arm resides, said spatula having an inward face that is concave and facing the gripping surface of the gripping tip on the first forceps arm, the inward face of the spatula having a length from a proximal edge of the spatula to a front edge of the spatula that is greater than a height of the inward face;
wherein said gripping plane passes through the proximal edge and the front edge of the spatula when the forceps are fully closed; and the direction in which the gripping tip moves inward towards the opposing inward face of the spatula lies in the gripping plane and the spatula is straight along a gripping plane when the forceps are fully closed; and
further wherein the inward face of the spatula comprises a trough for the article and the gripping surface of the gripping tip between the base and the front portion of the gripping tip is adapted to hold the article against the trough of the concave inward face of the spatula when the forceps arms are fully closed with the article placed on the spatula; and the front edge of the spatula is round when viewed from a side elevation of the forceps along the gripping plane and the front edge of the inward face of the spatula extends forward from the front portion of the tip on the opposing arm.

11. The forceps recited in claim 1 wherein the thickness of a distal portion of the spatula is no greater than about 0.5 mm.

12. The forceps recited in claim 10 wherein the gripping tip is oriented at an obtuse angle with respect to the first forceps arm and the spatula is oriented at the same obtuse angle with respect to the second forceps arm.

13. The forceps recited in claim 10 wherein the forceps is autoclavable.

14. The membrane placement forceps recited in claim 10 wherein the spatula also has an outward face that is generally parallel to the inward face, wherein the spatula has a proximal portion having a local maximum height of A' and a distal portion having a local maximum height of A, and a minimum height D of the spatula is located between the distal portion and the proximal portion, such that A is greater than D and A' is greater than D.

15. The membrane placement forceps recited in claim 14 wherein the height A is greater than the height A'.

16. The membrane placement forceps recited in claim 1 wherein a radius of curvature for the concave inward face of the spatula is between 10 cm and 2.5 cm.

17. The membrane placement forceps recited in claim 1 wherein the gripping surface on the gripping tip (16, FIG. 5) is perpendicular to the gripping plane (28, FIG. 5) when the forceps are fully closed.

18. The membrane placement forceps recited in claim 1 wherein the spatula (14) is fixed on the second forceps arm so that the inward face (18, FIG. 5) is oriented generally perpendicular to the gripping plane (28, FIG. 5).

19. A membrane placement forceps for regenerative osseous surgery in dentistry, the forceps comprising:
a pair of elongated forceps arms activated with finger pressure, the pair comprising a first forceps arm and a second forceps arm attached together at a proximal end and free at a distal end;
a gripping tip on the distal end of the first forceps arm, said gripping tip having a gripping surface extending along a gripping plane from a base of the gripping tip to a front portion of the gripping tip; and
a spatula for assisting in the placement of a membrane to block out soft tissue growth during regenerative osseous surgery, the spatula being statically secured on the distal end of the second forceps arm in a fixed orientation and extending generally in a plane in which the linear direction of the elongated second forceps arm resides, said spatula having an inward face that is concave and facing the gripping surface of the gripping tip on the first forceps arm, the inward face of the spatula having a length from a proximal edge of the spatula to a front edge of the spatula that is greater than a height of the inward face;
wherein said gripping plane passes through the proximal edge and the front edge of the spatula when the forceps are fully closed, and the direction in which the gripping tip moves inward towards the opposing inward face of the spatula lies in the gripping plane and the spatula is straight along the gripping plane when the forceps are fully closed;
further wherein the inward face of the spatula comprises a trough for the membrane and the gripping surface of the gripping tip between the base and the front portion of the gripping tip is adapted to hold the membrane against the trough of the concave inward face of the spatula when the forceps arms are fully closed with the membrane placed on the spatula, and the front edge of the spatula is round when viewed from a side elevation of the forceps along the gripping plane and the front edge of the inward face of the spatula extends forward from the front portion of the tip on the opposing arm.

\* \* \* \* \*